United States Patent [19]

Hakky et al.

[11] Patent Number: 5,498,258

[45] Date of Patent: Mar. 12, 1996

[54] LASER RESECTOSCOPE WITH LASER INDUCED MECHANICAL CUTTING MEANS

[76] Inventors: Said I. Hakky, 8547 Merrimoor Blvd., E, Largo, Fla. 34647-3145; Perry B. Hudson, 2225 Park St., North, St. Petersburg, Fla. 33710

[21] Appl. No.: 306,186

[22] Filed: Sep. 13, 1994

[51] Int. Cl.⁶ ...................................... A61B 17/36
[52] U.S. Cl. .............. 606/15; 606/16; 606/170; 604/22
[58] Field of Search .............. 604/21, 22; 606/13, 606/14, 15, 28, 127, 128, 170, 180, 7, 10, 11, 12, 15, 27, 167–171

[56] References Cited

U.S. PATENT DOCUMENTS

| | | | |
|---|---|---|---|
| 4,631,052 | 12/1986 | Kensey | 604/22 |
| 4,694,828 | 9/1987 | Eichenbaumm | 606/14 |
| 4,955,882 | 9/1990 | Hakky | 606/14 |
| 5,201,731 | 4/1993 | Hakky et al. | 606/15 |
| 5,312,397 | 5/1994 | Hakky et al. | 606/15 |

Primary Examiner—Stephen C. Pellegrino
Assistant Examiner—Michael Peffley
Attorney, Agent, or Firm—John Lezdey

[57] ABSTRACT

The present invention provides a device and method for coagulating, lasing, resecting and removing prostate and bladder tissue. The device is a laser resectoscope containing laser induced mechanical cutting. The tips of the cutting blades are coated with Teflon and Stainless Steel to prevent adherence of the lased or resected tissue. The contact laser head and cutting blades are heated by a laser beam. This allows the operator to lase and resect the targeted tissue without impairing the cellular integrity of the tissue. Consequently, the retrieved tissue is preserved for histological analysis.

A method is also provided to coagulate, lase, resect and remove tissue from the prostate and bladder areas using the above mentioned laser resectoscope with laser induced heating.

12 Claims, 2 Drawing Sheets

LASER RESECTOSCOPE WITH LASER INDUCED MECHANICAL CUTTING MEANS

FIELD OF THE INVENTION

The present invention relates to a surgical device and method for coagulating, lasing, resecting and removing tissue in a patient and in particular, a laser resectoscope with laser induced mechanical cutting means.

BACKGROUND OF THE INVENTION

A resectoscope device is employed transurethrally to perform prostate and bladder surgery. This device has an elongated outer cylinder usually made from stainless steel, which is inserted in the urethra. Inside the cylinder, a working element is employed to remove the desired tissue using diathermy coagulation. The outer elongated cylinder prevents the urethra from collapsing while the desired tissue is removed.

The current method to remove a benign or cancerous prostate or bladder tumor is called Transurethral Resection of the Prostate or Transurethral Resection of Bladder Tumor. The conventional method uses diathermy coagulation to heat a conductive wire in order to cut the desired tissue. The surgeon manually extends the cutting wire loop beyond the end of the outer sheath to a position engaging the tissue to be cut. Thereafter, the cutting element is electrically energized through the actuation of the diathermy unit. The resected piece of tissue is pushed into the bladder by the continuous flow of fluids from a reservoir through the resectoscope. The surgeon views the target area through a telescopic system. A continuous irrigation system is utilized to keep the line of sight free of blood, debris and resected tissue. During prostate surgery it is common to cut away between one half and one gram of tissue each minute. It is quite common to remove 20–100 grams of prostate during a single procedure.

A 5% glycine solution is commonly used during transurethral resection of the prostate or bladder tumor. This fluid is isoosmotic, but has the disadvantage of overloading the circulatory system causing cardiac complications. Furthermore, before the procedure is completed the bladder must be irrigated and emptied from the prostatic tissues debris, blood and fluid. It would, therefore, facilitate the procedure if the irrigation fluid is normal saline, which is more physiological. It would also facilitate the procedure if the irrigation fluids, blood clots and tissue debris could be removed without having to irrigate the bladder.

In the diathermy unit previously described, electricity is used both to cut and coagulate the tissue. The exact depth of the resection cannot be gauged in diathermy coagulation. Moreover, this type of procedure has a tendency to produce scarring and retrograde ejaculation.

The use of the laser is replacing the conventional resectoscope because it allows the use of normal saline. The laser produces less scarring, and reduces the risk of retrograde ejaculation.

U.S. Pat. No. 5,312,399 issued to Hakky and incorporated herein, shows a modern laser resectoscope with electrically induced mechanical cutting means and laser coagulating means.

There are two types of laser delivering systems: non-contact and contact.

In the non-contact laser, a fiber optic with a 400–600 micron diameter is used to deliver the laser at a distance of a few centimeters from the desired area. The laser coagulates or carbonizes the tissue depending on the amount of wattage used and the duration of laser delivery. The tissue coagulates at 55–90° Celsius and start to vaporize or carbonize at temperatures exceeding 100° degrees Celsius. U.S. Pat. Nos. 4,955,882 and 5,312,399 (Hakky) disclose a resectoscope device embodying a laser for use in coagulation and removal of the prostate and bladder tissue. A cutting blade is provided in that device for cutting away tissue which had been coagulated by the laser. The tissue is either side or end lased, e.g., the laser is directed at a right angle to the laser delivery fiber, or at the tip of the laser delivery fiber respectively. Another laser device on the market is offered by Intra-Sonix, Inc. of Burlington, Massachusetts for affecting what it refers to as "transurethral ultrasound guided laser induced prostatectomy" (TULIP). This device utilizes a laser mounted on an ultrasound transducer introduced transurethrally to heat the prostate tissue to the point that it becomes necrotic, that is, the living prostate tissue becomes pathologically dead. The necrotic tissue sloughs off and is expelled in the patient's urine over an extended period of weeks or months following the procedure.

In the contact laser, a probe made of sapphire or quartz is employed to deliver the laser energy by direct contact of the laser probe with the desired tissue. Certain disadvantages are encountered in the current contact laser ablation. These disadvantages include adherence of the tissues to the tip of the probe, prolonged procedure times, high temperatures needed for tissue vaporization, and the destruction of tissue that is needed for histological diagnosis. Surgical Laser Technologies of Oaks, Pennsylvania offers a "contact laser". The probes in this laser can only be utilized for benign prostate tissues. Moreover, no tissue can be removed for histological examination. As explained above, the patient is expected to expel the necrotic tissue left behind in a matter of weeks or months.

There are some principal disadvantages in the prior art. In both the non-contact and contact laser delivery systems described above, tissue is not removed for histological evaluation. Furthermore, once necrosis sets in, the tissue is left to slough spontaneously. This can cause infection, scarring and urinary retention.

SUMMARY OF THE INVENTION

The present invention provides a device and method for coagulating, lasing, resecting and removing body tissue, especially, prostate and bladder tissue using a laser resectoscope with laser induced mechanical cutting means. The device contains an elongated outer cylinder housing which is shaped at the distal or working end to allow it to be introduced into a living being. The working elements of the device are provided inside the housing and include: a rotatable laser directing means which directs a laser beam from an external laser producing source, a rotatable laser head at the distal end, and cutting blades attached thereto. Furthermore, a motor means is provided for rotating the laser directing means.

Advantageously, there are at least three lumens inside the cylinder-one for introducing fluids, one for withdrawing fluids and resected tissue, and one for holding the laser means and other optical fibers.

The device is configured to accept either a contacting or non-contacting laser head. This head is attached to the laser fiber. In the case of the contact procedure, the head is connected to the end of an insulated rotating laser shaft. Laser light, which is non-polarizing, is provided for activating and heating the contact head and associated cutting blades. Once heated, the head and blades can coagulate, lase and resect, if desired, a tissue portion without impairing the integrity of the tissue's cellular architecture. Thus, the resected tissue is available for histological analysis. Of course, the device can also be used to vaporize the tissue, if desired.

Other embodiments of the device include various optical imaging means that allow illumination and visualization of the procedure, suction means to facilitate removal of the resected tissue, and an air driven and button activated motor means. Advantageously, an irrigation fluid is used, and more advantageously, the irrigation fluid it is a saline solution.

Finally, a method is also provided for coagulating, lasing, resecting and removing tissue from a patient using a device as the present invention describes herein.

OBJECTS OF THE INVENTION

Accordingly, it is the general object of this invention to provide an apparatus and a method of use which overcomes the disadvantages of the prior art.

It is a further object of this invention to provide an apparatus and method of use which enables the resection of tissue by means of laser, yet which also facilitates the retrieval of lased tissue for histological examination.

It is still a further object of this invention to provide an apparatus and method of use which increases the speed, efficiency and safety, while decreasing the cost of endoscopic prostate and bladder surgery.

It is an additional object of this invention to provide a resectoscope utilizing contact and non-contact lasers to partly coagulate and partly vaporize the prostate or bladder tissue, such preservation allows for retrieval of the tissue for histological examination.

It is yet another object of the invention to provide a rotating contact laser probe with a Teflon coating to prevent tissue adherence and speed the time of surgery.

It is still a further object of this invention to provide a laser resectoscope for coagulation and vaporization of tissue, efficient resection of the coagulated tissue, an irrigation and suction means for the removal of resected tissue, and irrigation on continuous basis.

DESCRIPTION OF THE PREFERRED EMBODIMENTS

Figure 1:
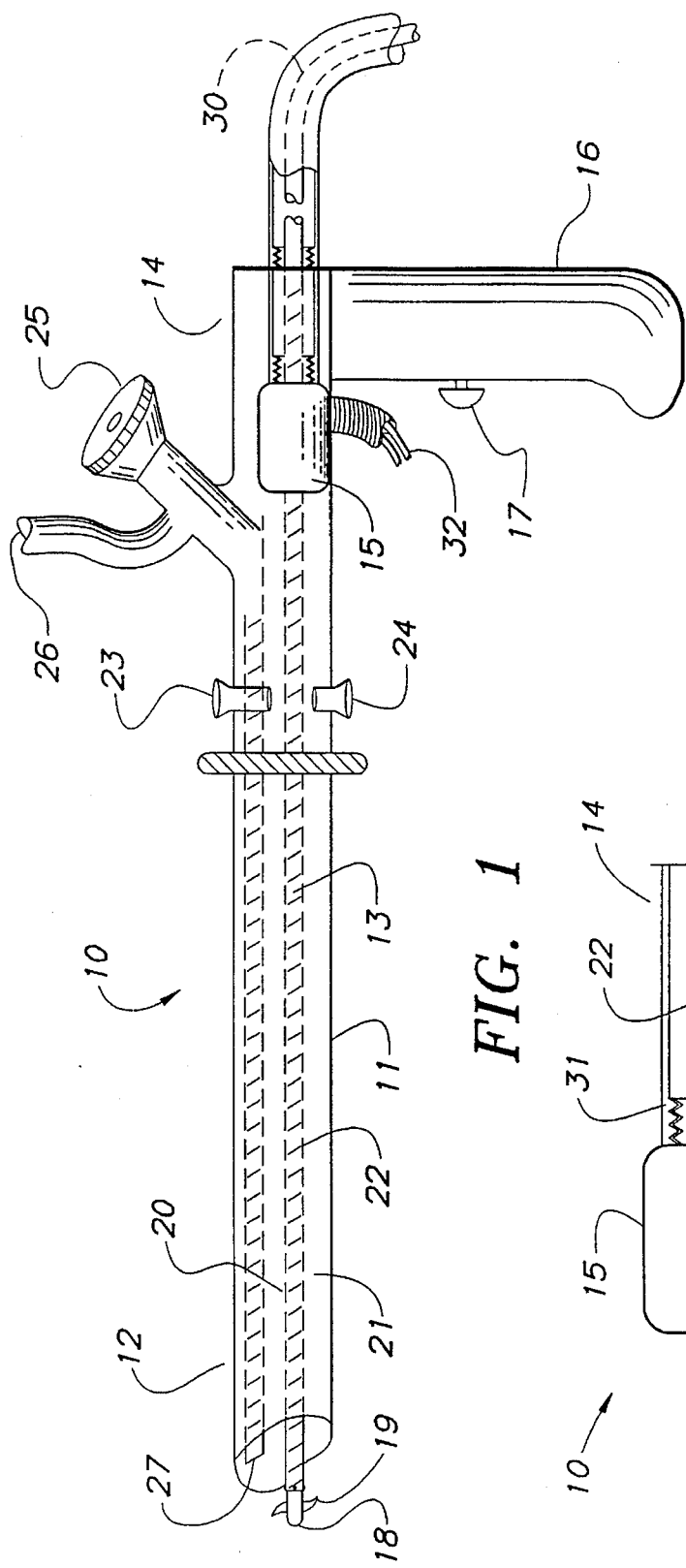
FIG. 1 is a horizontal side view of the laser resectoscope with laser induced mechanical cutting means.

Although specific terms are used in the following description for the sake of clarity, these terms are intended to refer only to the particular structure of the invention selected for illustration in the drawings and are not intended to define or limit the scope of the invention.

FIG. 1 illustrates a horizontal side view of the present invention. The laser resectoscope 10 has an elongated cylinder 11 along the entire length of the resectoscope 10. The cylinder 11 is shaped at the distal or working end 12 of the resectoscope 10 to allow introduction into a patient.

Inside the cylinder 11 is a rotatable laser directing means 13 for directing a laser beam 30 from an external laser producing source located near the proximal or operator end 14 of the resectoscope 10. A motor means, preferably an air driven micromotor 15, is situated near the proximal end 14 and is used to rotate the laser direction means 13.

Advantageously, a cylindrical hand grip 16 is attached to the resectoscope 10 near the micromotor. While the resectoscope 10 may be fitted to a foot pedal to activate the micromotor, it is advantageous to control the micromotor with a button switch 17 located on the hand grip 16.

At the distal end 12 of the resectoscope 10 is a contact laser head 18 having cutting blades 19 for resecting tissue. The laser beam heats the laser head and cutting blades to effect coagulation and resection of the tissue. Thus, the mechanical cutting means are laser induced.

The resectoscope 10 has at least three lumens. One lumen 20 is provided for the introduction of irrigating fluids and is connected to an inlet valve 23. Advantageously, the irrigation fluid is a saline solution. A second lumen 21 is provided for withdrawing fluids and solid tissues and is connected to an outlet valve 24. Suction means is connected to the withdrawing lumen 21 at the proximal end 14 to facilitate removal and collection of the resected tissue. The third lumen 22 houses the laser directing means 13 and fiber optics for illumination and visualization of the procedure.

Advantageously, the fiber optics are connected to an eye piece 25 near the proximal end 14. The eye piece 25 has a side opening 26 to allow the entry of light to illuminate the procedure. Advantageously, the eye piece 25 can be connected to a camera and monitor which gives the operator the option of viewing the procedure directly or through a monitor where the image is projected on.

The eye piece 25 and fiber optic system includes a series of complex prisms and lenses 27 and are aligned at the distal end 12 so as to give the operator a 30 degree angle view of the procedure looking downward from the horizontal axis.

Figure 2:
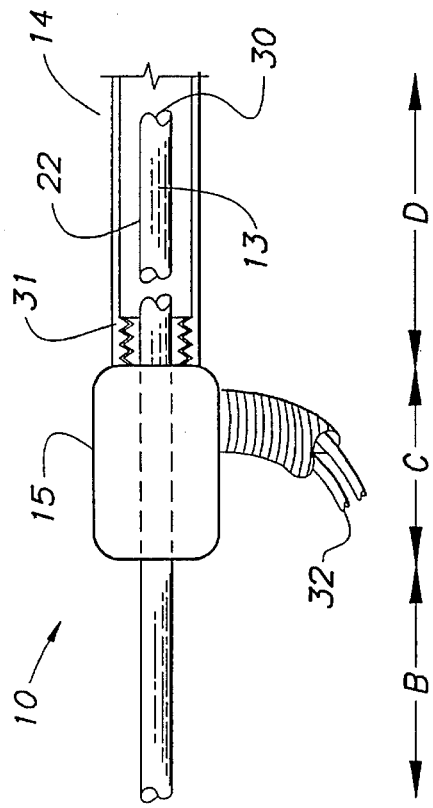
FIG. 2 is a horizontal side view of the operator or proximal end of the laser resectoscope.
Figure 3:
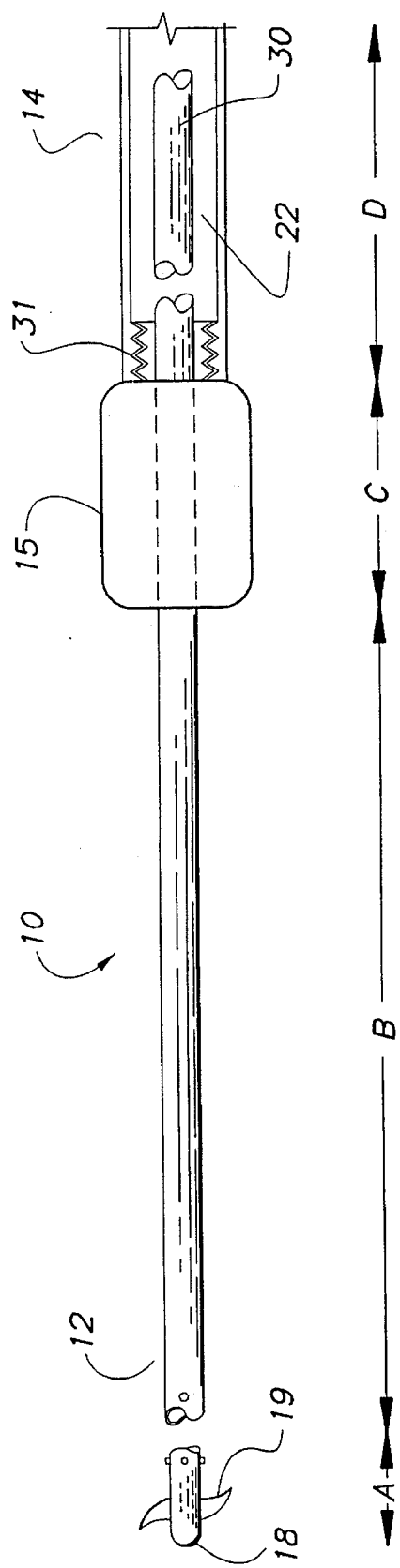
FIG. 3 is another horizontal side view of the laser resectoscope.

FIG. 2 shows a horizontal side view of the proximal end 14 of the laser resectoscope 10. A laser cable is screwed onto the proximal end 14. An external laser source emits a laser beam 30 through the lumen 22. An enlargened view of the air micromotor 15 is illustrated in FIG. 3. The micromotor 15 rotates the laser directing means 13. The lumen 22 housing the laser is connected to the micromotor 15 via a screw-on connector 31. The micromotor has a valve system 32 containing inlet and outlet valves which are connected to an air compressor. The valve system 32 reduces air noise.

FIG. 3 is another horizontal view of the laser resectoscope 10. Illustrated at the proximal end 14 are the laser beam 30, lumen 22 housing the laser beam 30, air micromotor 15, and screw on connector 31 for connecting the lumen 22 with the motor 15. Also illustrated are the removable rotating contact laser head 18 and cutting blades 19.

Figure 4:
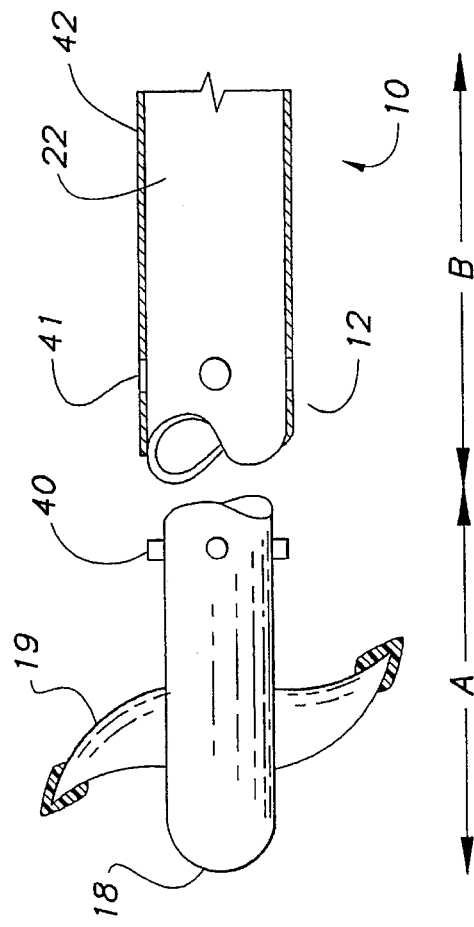
FIG. 4 is a horizontal side view of the working or distal end of the laser resectoscope.

A more detailed picture of the removable contact laser head 18 is provided in FIG. 4. The head 18 may be snapped onto the insulated rotating laser shaft at the distal end 12 of the resectoscope 10 by way of a snap-in button 40 and apertures 41. The lumen 22 housing the laser beam is insulated 42. The irrigation fluid is introduced and bathes the energized insulated laser shaft.

The contact laser head 18 is made out of sapphire or quartz. Attached to the head 18 are at least two cutting blades 19 approximately 8 to 12 mils in length. The shape of each blade 19 resembles a shallow curved ice-cream scoop. The tip of each blade 19 is coated with stainless steel and Teflon to prevent adhesion of lased or resected tissue.

Advantageously, the introduction means is shaped at the distal end so that the introduction means can be configured through the urethra and into the prostate or bladder area.

The laser induced heating of the contact head 18 and cutting blades 19 allows the operator to lase and resect tissue without impairing the cellular integrity of the tissue cells. Consequently, the retrieved tissue is preserved for histological analysis.

In the method taught in this patent, a well lubricated elongated outer cylinder of the resectoscope is inserted urethrally into the prostate or bladder area. The working elements are connected inside the cylinder. The outer sheath of the cylinder prevents the urethra from collapsing. The laser cable from the laser source is screwed tightly on the operator or proximal end of the resectoscope. A saline fluid reservoir is connected to the inflow fluid valve. The out-flow fluid is connected to a suction machine which provides continuous negative pressure in the area where the prostate or the bladder is resected. A rotatable contact head having cutting blades is snapped on at the end of the insulated rotating laser shaft.

Standard laser precaution for the staff is taken, like the wearing of protective eye wear. The laser is switched on. The button on the handle of the resectoscope is pressed, which activates the micromotor. The saline fluid and the suction machine is switched on. The contact laser head is energized with laser and becomes very hot. The rotating cutting blades resect the prostate or bladder tissue. The blood, fluid and tissue debris are sucked through the out valve and into the suction machine. The Teflon coated stainless steel tip prevents the resected tissue from sticking to the resecting cutting blades. This method is called Contact Laser Prostatectomy. If the surgeon prefers a side firing free beam, then he/she can remove the rotating insulated laser shaft and insert the rotating twin blades described in U.S. Pat. No. 5,312,399. The surgeon can also use a 400–600 micron side firing laser fiber.

This laser resectoscope can resect both benign or cancerous prostate. It can also be utilized to resect bladder tumors.

Although the invention has been described with a certain degree of particularity, it is understood that the present disclosure has been made only by way of example and that numerous changes in the details of construction and the combination and arrangement of parts may be resorted to without departing from the spirit and scope of the invention.

What is claimed is:

1. A laser resectoscope for coagulating, lasing, resecting and removing tissue from a patient, said device comprising:

a) an elongated cylinder, said cylinder having at the distal end a means for introduction into said patient;

b) rotatable means for directinq a beam of laser radiation within said cylinder from a source of laser radiation;

c) a laser beam contacting head at the distal end of said laser directing means and rotating therewith, said contact laser head having cutting blades for cutting away tissue;

d) motor means at the proximal end of said cylinder for rotating said laser directing means; and e) means within said cylinder for removing resected tissue, whereby said laser beam heats said laser beam contacting head and said cutting blades.

2. The resectoscope of claim 1 including at least three lumens within said cylinder, wherein one lumen allows for the introductions of fluids, a second lumen allows for the withdrawal of fluids and solids, and a third lumen allows for housing the laser directing means.

3. The resectroscope of claim 2 including suction means connected to said second lumen to facilitate removal and collection of said tissue.

4. The resectroscope of claim 2 including a source of irrigation fluid for passing through said introducing lumen.

5. The resectoscope of claim 1 wherein said laser beam contact head is made from sapphire or quartz, and wherein the tip of said cutting blades consist of Teflon coated stainless steel.

6. The resectoscope of claim 1 wherein said laser beam contact head is removable from said laser directing means.

7. The resectoscope of claim 2 including suction means connected to said second lumen to facilitate removal and collection of said tissue.

8. The resectoscope of claim 2 including a source of irrigation fluid for passing through said introducing lumen.

9. The resectoscope of claim 1 wherein said motor means comprises an air driven micromotor.

10. A method of coagulating, lasing, resecting and removing tissue from the prostate or bladder of a patient, said method comprising the steps of:

a) introducing elongated means through the urethra of a patient to the bladder or prostrate site, said elongated means having a rotatable contact head with cutting blades;

b) providing a laser beam;

c) heating said contact head and blades with said laser beam;

d) simultaneously coagulating, lasting and resecting a tissue portion without impairing the integrity of the tissue's cellular architecture with said contact head and cutting blades;

e) irrigating the site of lasing and resecting with irrigating fluid; and then f) removing said irrigating fluid and resected tissue.

11. The method of claim 10 including visually monitoring the coagulation, lasing and resecting of said tissue portion.

12. The method of claim 10 wherein said irrigating fluid is a saline solution.

\* \* \* \* \*